(12) United States Patent
He et al.

(10) Patent No.: US 11,982,596 B2
(45) Date of Patent: May 14, 2024

(54) METHOD AND SYSTEM FOR BLAST-INDUCED VIBRATION MONITORING OF TUNNELS IN HIGH ASYMMETRIC IN-SITU STRESSES

(71) Applicant: Northeastern University, Shenyang (CN)

(72) Inventors: Benguo He, Shenyang (CN); Xiating Feng, Shenyang (CN); Jie Wang, Shenyang (CN); Shichen Qiu, Shenyang (CN); Xiangrui Meng, Shenyang (CN); Lei Wang, Shenyang (CN)

(73) Assignee: NORTHEASTERN UNIVERSITY, Shenyang (CN)

( * ) Notice: Subject to any disclaimer, the term of this patent is extended or adjusted under 35 U.S.C. 154(b) by 0 days.

(21) Appl. No.: 18/547,754

(22) PCT Filed: Nov. 25, 2022

(86) PCT No.: PCT/CN2022/134329
§ 371 (c)(1),
(2) Date: Aug. 24, 2023

(87) PCT Pub. No.: WO2023/202074
PCT Pub. Date: Oct. 26, 2023

(65) Prior Publication Data
US 2024/0044740 A1    Feb. 8, 2024

(30) Foreign Application Priority Data

Apr. 21, 2022  (CN) .......................... 202210420392.1

(51) Int. Cl.
*G01M 7/08*  (2006.01)
*G01N 3/313*  (2006.01)
*G01N 33/24*  (2006.01)

(52) U.S. Cl.
CPC .............. *G01M 7/08* (2013.01); *G01N 3/313* (2013.01); *G01N 33/24* (2013.01)

(58) Field of Classification Search
CPC .......... G01N 3/313; G01N 33/24; G01M 7/08
See application file for complete search history.

(56) References Cited

U.S. PATENT DOCUMENTS

| | | | |
|---|---|---|---|
| 2014/0365143 A1* | 12/2014 | Henley ................. | G01H 17/00 702/39 |
| 2020/0041643 A1* | 2/2020 | Kimchy ................. | G01S 15/32 |
| 2022/0244155 A1* | 8/2022 | Ma ........................ | G01V 1/008 |

FOREIGN PATENT DOCUMENTS

| CN | 103697999 A | 4/2014 |
|---|---|---|
| CN | 107165678 A | 9/2017 |

(Continued)

OTHER PUBLICATIONS

Machine translation of CN110219655 (Year: 2019).*

(Continued)

*Primary Examiner* — Natalie Huls
(74) *Attorney, Agent, or Firm* — Muncy, Geissler, Olds & Lowe, P.C.

(57) ABSTRACT

The invention provides a method and system for a blast-induced vibration monitoring of a tunnel in high asymmetric in-situ stresses. According to the method, triaxial vibration sensors are respectively fixed in areas having different radial depths inside surrounding rocks of a stress concentration area behind a tunnel face of the tunnel in high asymmetric in-situ stresses, and each triaxial vibration sensor monitors blast vibration velocity and acceleration at a position thereof. The system comprises a plurality of triaxial vibration sensors which are fixed in areas having different radial depths inside surrounding rocks of a stress concentration area behind a tunnel face of the tunnel in high asymmetric in-situ stresses, and each triaxial vibration sensor is used for (Continued)

monitoring blast vibration velocity and acceleration at a position thereof. The method and system can improve the safety and the efficiency of tunnel excavation construction.

5 Claims, 7 Drawing Sheets

(56) References Cited

FOREIGN PATENT DOCUMENTS

| CN | 107238538 A | 10/2017 |
|---|---|---|
| CN | 107478523 A | 12/2017 |
| CN | 109239779 A | 1/2019 |
| CN | 208858408 U | 5/2019 |
| CN | 110219655 A | 9/2019 |
| CN | 114964469 A | 8/2022 |
| JP | H1137834 A | 2/1999 |

OTHER PUBLICATIONS

Machine translation of CN107238538 (Year: 2017).*
Zhang Xiong et al., "Study of Blasting Vibration Control Technology on Tunnel at Soil-Rock Boundary Stratum", Highway Engineering, vol. 45, No. 4, Aug. 20, 2020, pp. 162-166.
Ding Yuanzhen et al., "Study on deformation characteristics of soft rock tunnel in fault zone with high geostress and control measures", China Civil Enginee Ing Jou Nal, vol. 50, No. S1, Jul. 15, 2017, pp. 129-134.
Shen Zhi et al., "Research on Blasting Vibration Tests of Cave Depot Project", Soil Eng. and Foundation, vol. 22, No. 02, Apr. 15, 2008, pp. 75-77.
Xu Jiang-bo et al., "Research on Blasting Vibration of Luosha Tunnel Entrance", Science Technology and Engineering, vol. 16, No. 09, Mar. 28, 2016, pp. 93-98.

* cited by examiner

METHOD AND SYSTEM FOR BLAST-INDUCED VIBRATION MONITORING OF TUNNELS IN HIGH ASYMMETRIC IN-SITU STRESSES

BACKGROUND OF THE INVENTION

1. Field of the Invention

The invention relates to the technical field of tunnel engineering, in particular to a method and system for a blast-induced vibration monitoring of a tunnel in high asymmetric in-situ stresses.

2. The Prior Arts

Geostress is a natural stress that exists in strata and is not disturbed by engineering activities. Due to the coupling effect of multiple tectonic movements, surface sedimentation and erosion, a three-dimensional virgin rock stress field of deep engineering rock masses is complex. Deep-buried tunnels are mainly positioned in a constantly-changing three-dimensional high geostress (maximum principal stress $\sigma_1$>intermediate principal stress $\sigma_2$>minimum principal stress $\sigma_3$), and long-term strong tectonic activity, and the principal direction of geostress usually does not coincide with a tunnel coordinate system. The stress distribution is often asymmetrical across the cross section of a tunnel, and the surrounding rocks of the stress concentration area around the tunnel are easy to be destroyed, higher in energy, and more obvious to be affected by blasting of a tunnel face, so that the surrounding rocks of the stress concentration area around the tunnel are the key part of tunnel stability control.

With the advance of the tunnel face, the surrounding rocks behind the tunnel face of the high stress tunnel gradually increases in the tangential stress, and decreases in the radial stress, the stress difference increases, and the surrounding rocks are gradually in the unfavorable stress state. At this time, during blast excavation of the tunnel face of the deep-buried tunnel, blast stress waves cause a vibration of the surrounding rocks, which easily induces fracture of rock masses. When local stress concentration degree is high enough, even dynamic disasters such as rock bursts can be caused.

Nowadays, a drilling and blasting method has the characteristics of being low in cost, low in dependence on large machinery, capable of operating with simple machinery, and effective under various geological conditions, so that the drilling and blasting method is widely used in the excavation of most highway tunnels and mountain tunnels. The experience shows that the stress concentration area is formed in the surrounding rocks in the direction vertical to the connecting line of the maximum principal stress borne by the cross section of the tunnel behind the tunnel face. The stress concentration area is easy to be influenced by the stress wave vibration generated by blasting construction of the tunnel face and is an important part for monitoring the influence of a blast vibration.

At present, a geometric symmetry method is used for monitoring the blast vibration of the tunnel face, which does not consider the characteristics of the stress concentration area of the asymmetric high stress tunnel, and the monitoring part is often inconsistent with the vulnerable part of the stress concentration area, so that the stability of the surrounding rocks cannot be effectively evaluated. Second, after the excavation of a high stress tunnel, the inner parts of the surrounding rocks in the stress concentration area will be damaged, the bearing capacity will decrease, the characteristics of energy accumulation and release are different, and the types of rocks generating deep disasters are different. The tunnel walls are mostly subjected to brittle tensile failure. As the distance between the inner parts of the surrounding rocks and the tunnel walls increases, the inner parts of the surrounding rocks gradually transition from brittle tensile failure to ductile shear failure, which has different effects on the blast vibration. The existing methods for the blast-induced vibration monitoring do not consider the stress concentration area caused by asymmetric high stress in the aspects of drilling position and depth, and cannot effectively monitor fracture caused by damage of the blast vibration to the surrounding rocks.

SUMMARY OF THE INVENTION

The existing methods for the blast-induced vibration monitoring do not consider the surrounding rocks in the stress concentration area caused by asymmetric high stress in deep-buried tunnels, and the blasting of the tunnel face is prone to triggering the failure and instability of the surrounding rocks in the area. Aiming to solve the above problems, the invention provides a method and system for a blast-induced vibration monitoring of a tunnel in high asymmetric in-situ stresses. Compared with the prior art, the method and system can focus on monitoring the blast vibration velocity and acceleration of different radial depths in the stress concentration area, improve the safety and efficiency of tunnel excavation construction, and ensure the safety of construction personnel and equipment.

The invention adopts the following technical solution.

The first aspect of the invention provides a method for a blast-induced vibration monitoring of a tunnel in high asymmetric in-situ stresses. Triaxial vibration sensors are respectively fixed in areas having different radial depths inside surrounding rocks of a stress concentration area behind a tunnel face of the asymmetric high stress tunnel, and each triaxial vibration sensor monitors blast vibration velocity and acceleration at a position of the triaxial vibration sensor.

According to the method for the blast-induced vibration monitoring of the tunnel in high asymmetric in-situ stresses, the method comprises the following steps.

Step 1: determining a position of the stress concentration area behind the tunnel face of the tunnel in high asymmetric in-situ stresses, and the different radial depths inside the surrounding rocks of the stress concentration area.

Step 2: forming a plurality of drill holes extending from tunnel walls to inner parts of the surrounding rocks in the stress concentration area behind the tunnel face.

Step 3: fixing the triaxial vibration sensors respectively in the area having the different radial depths in each drill hole.

Step 4: collecting and storing the blast vibration velocity and acceleration measured by each triaxial vibration sensor at the position of the triaxial vibration sensor.

According to the method for the blast-induced vibration monitoring of the tunnel in high asymmetric in-situ stresses, based on geological data of the surrounding rocks of the tunnel in high asymmetric in-situ stresses, the position of the stress concentration area of a cross section behind the tunnel face of the tunnel in high asymmetric in-situ stresses and the different radial depths inside the surrounding rocks of the stress concentration area are determined according to a geostress distribution of asymmetric virgin rocks and geometric characteristics of the cross section of the tunnel in high asymmetric in-situ stresses.

According to any of the methods for the blast-induced vibration monitoring of the tunnel in high asymmetric in-situ stresses, the different radial depths are depths at three places of surface layers, inward surface layers and deeper layers inside the surrounding rocks of the stress concentration area.

According to the method for the blast-induced vibration monitoring of the tunnel in high asymmetric in-situ stresses, five drill holes of $1^\#$, $2^\#$, $3^\#$, $4^\#$ and $5^\#$ are formed in a row at an interval of 10 m in a middle position of the stress concentration area behind the tunnel face.

According to the method for the blast-induced vibration monitoring of the tunnel in high asymmetric in-situ stresses, a first drill hole away from the tunnel face is 2 times a tunnel span.

According to the method for the blast-induced vibration monitoring of the tunnel in high asymmetric in-situ stresses, the step of fixing the triaxial vibration sensors in the area having the different radial depths in each drill hole comprises steps of mixing hole drilling debris with cement and water to form a sealing material, and using a pump to transport the sealing material to the drill holes to seal the triaxial vibration sensors, so that the triaxial vibration sensors are integrated with the inner parts of the surrounding rocks of the tunnel in high asymmetric in-situ stresses to ensure that the triaxial vibration sensors and the surrounding rocks of the tunnel in high asymmetric in-situ stresses are consistent in the blast vibration velocity and acceleration.

The second aspect of the invention provides a system for a blast-induced vibration monitoring of a tunnel in high asymmetric in-situ stresses. The system comprises a plurality of triaxial vibration sensors which are fixed in areas having different radial depths inside surrounding rocks of a stress concentration area behind a tunnel face of the tunnel in high asymmetric in-situ stresses, wherein each triaxial vibration sensor is used for monitoring blast vibration velocity and acceleration at a position of the triaxial vibration sensor.

The system for the blast-induced vibration monitoring of the tunnel in high asymmetric in-situ stresses as described above further comprises a cloud platform which is used for collecting and storing the blast vibration velocity and acceleration measured by each triaxial vibration sensor at the position of the triaxial vibration sensor.

The method and system disclosed by the invention have the following beneficial effects.

The method and system of the invention focus on monitoring the blast vibration velocity and acceleration at different radial depths in the stress concentration area behind the tunnel face of the tunnel in high asymmetric in-situ stresses. By analyzing monitored data, blasting charging amount, the number of detonator segments, segment differences, drill-hole arrangement and other parameters can be controlled. If necessary, an excavation method may be adjusted. According to the blast vibration velocity and acceleration at different radial depths, corresponding support parameters, including the thickness of a surrounding rock grouting ring and the length of an anchor rod, can also be determined, the safety and the construction efficiency of tunnel excavation construction can be improved, and the safety of construction personnel and equipment can be ensured.

Figure 1:
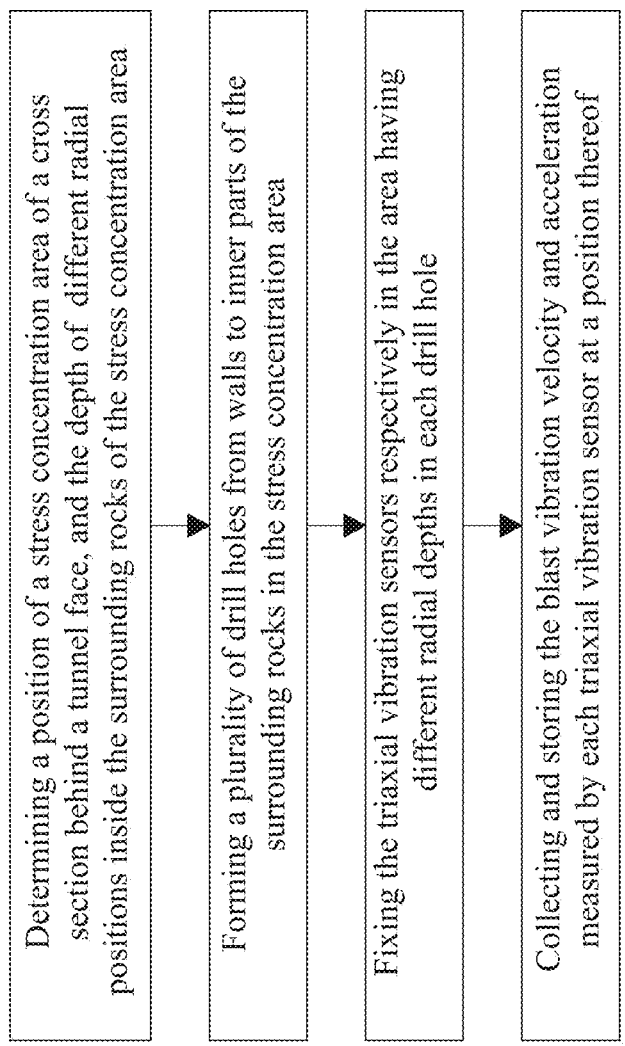
FIG. 1 is a schematic flow chart of a method for a blast-induced vibration monitoring of a tunnel in high asymmetric in-situ stresses according to an embodiment of the present invention.

In the drawings, $\sigma_1$, $\sigma_2$ and $\sigma_3$ are asymmetric maximum principal stress, intermediate principal stress and minimum principal stress, respectively; $1^\#$, $2^\#$, $3^\#$, $4^\#$ and $5^\#$ are respectively the positions of 5 drill holes; a, b and c are three different radial depths of the stress concentration area from the tunnel walls to the inner parts of the surrounding rocks, namely a surface layer, an inward surface layer and a deeper layer; and • indicates the installation positions of the triaxial vibration sensors.

DETAILED DESCRIPTION OF THE PREFERRED EMBODIMENT

The following further describes the invention with reference to the accompanying drawings and examples.

The first aspect of the invention provides a method for a blast-induced vibration monitoring of a tunnel in high asymmetric in-situ stresses. The method comprises the steps that triaxial vibration sensors are respectively fixed in areas having different radial depths inside surrounding rocks of the stress concentration area behind the tunnel face of the tunnel in high asymmetric in-situ stresses, and each triaxial vibration sensor monitors blast vibration velocity and acceleration at the position of the triaxial vibration sensor. FIG. 1 is a specific schematic flow chart of a method for a blast-induced vibration monitoring of a tunnel in high asymmetric in-situ stresses in the embodiment. As shown in FIG. 1, the method for the blast-induced vibration monitoring of the tunnel in high asymmetric in-situ stresses comprises the following specific steps.

Step 1: based on the geological data of the surrounding rocks of the tunnel in high asymmetric in-situ stresses, a position of the stress concentration area behind the tunnel face of the tunnel in high asymmetric in-situ stresses and the different radial depths inside the surrounding rocks of the stress concentration area are determined according to a geostress distribution of asymmetric virgin rocks and the geometric characteristics of the cross section of the tunnel in high asymmetric in-situ stresses.

Figure 2:
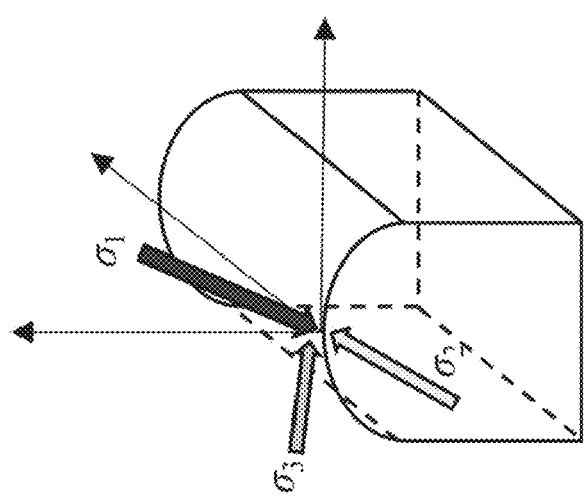
FIG. 2 is a diagram of a stress distribution of the tunnel in high asymmetric in-situ stresses.
Figure 3:
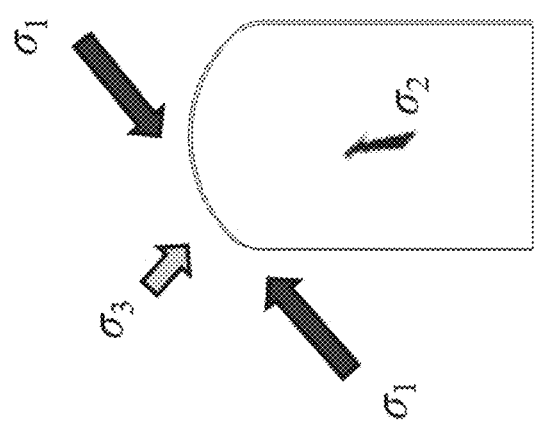
FIG. 3 is a diagram of a stress distribution of the tunnel in high asymmetric in-situ stresses.
Figure 4:
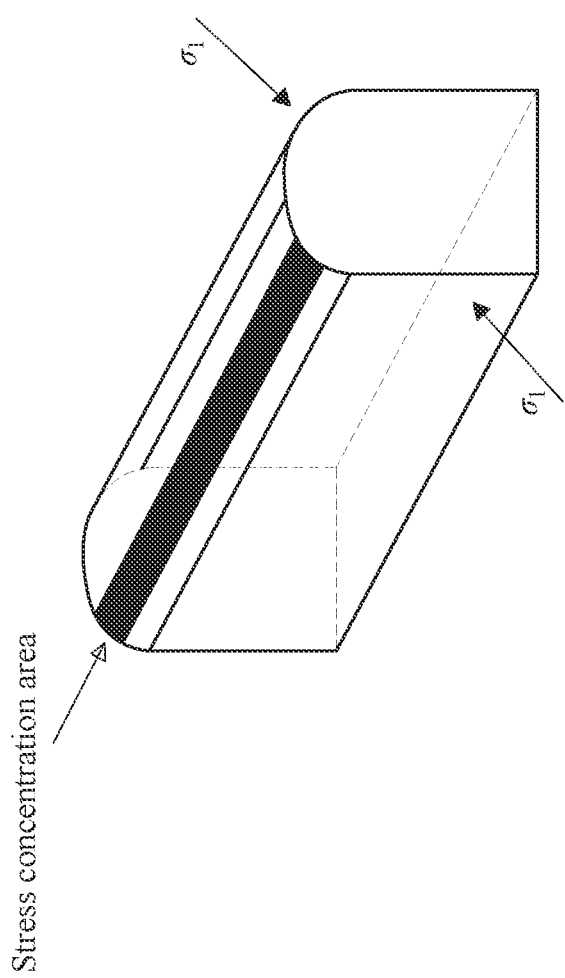
FIG. 4 is a schematic diagram of the position of a stress concentration area behind a tunnel face of the tunnel in high asymmetric in-situ stresses in the embodiment.
Figure 5:
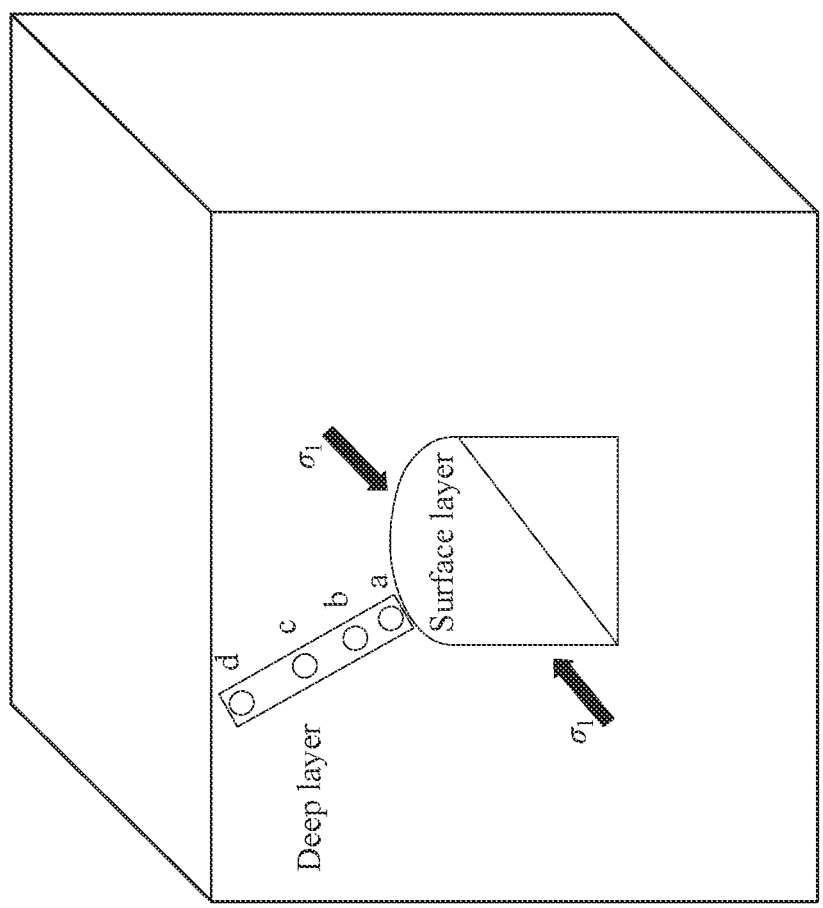
FIG. 5 is a schematic diagram of positions at different radial depths inside the surrounding rocks of the stress concentration area in the embodiment.

In the embodiment, firstly, the distribution of geostress during tunnel excavation is determined based on geological data of surrounding rocks of the tunnel in high asymmetric in-situ stresses, as shown in FIGS. 2 and 3; then, based on the distribution of the geostress and the spatial relationship with the geometry of the tunnel in high asymmetric in-situ stresses, the stress concentration area behind the tunnel face of the tunnel in high asymmetric in-situ stresses is obtained as shown in FIG. 4; and finally, based on the geological data of the surrounding rocks of the tunnel in high asymmetric in-situ stresses and relevant research, three depths of a surface layer point a, an inward surface layer point b, and a deeper layer point c of the surrounding rocks in the stress concentration area are determined as shown in FIG. 5.

Step 2: a plurality of drill holes extending from tunnel walls to the inner parts of the surrounding rocks are formed in the stress concentration area behind the tunnel face of the tunnel in high asymmetric in-situ stresses.

Figure 6:
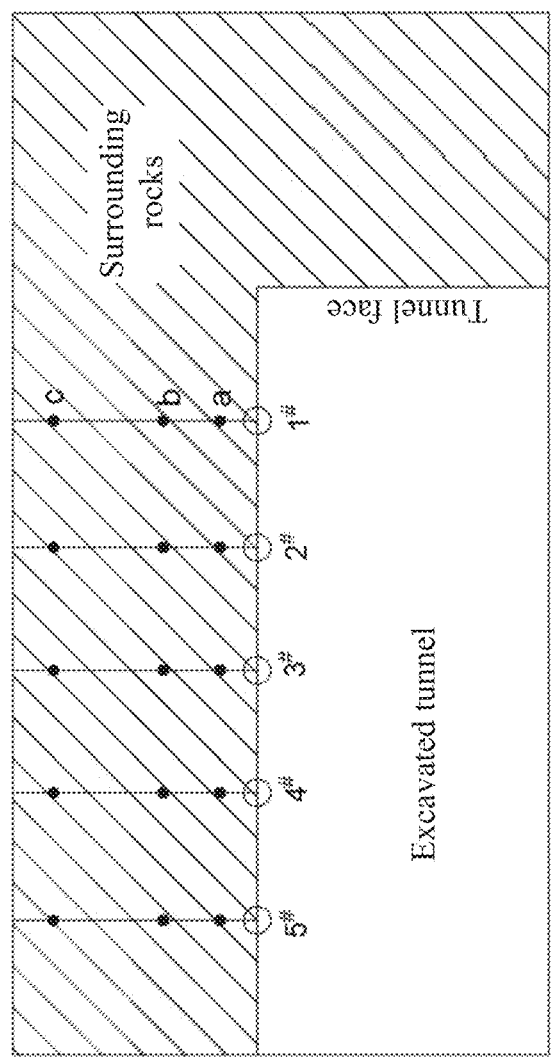
FIG. 6 is a schematic diagram of installation positions of triaxial vibration sensors in the embodiment.

In the embodiment, during blasting construction of the tunnel in high asymmetric in-situ stresses, as shown in FIG. 6, five drill holes of 1#, 2#, 3#, 4# and 5# are formed in a row at an interval of 10 m in the stress concentration area behind the tunnel face, and are located in a middle position of the stress concentration area behind the tunnel face, a first drill hole away from the tunnel face is 2 times a tunnel span, the diameter of the drill holes is slightly larger (such as 0.11 m-0.13 m) than the diameter of the triaxial vibration sensors, and the depth of the drill holes reaches a certain depth (such as 1 m) after reaching the deeper layer point c.

Step 3: the triaxial vibration sensors are respectively fixed in the area having the different radial depths in each drill hole.

Because the vibration of the surrounding rocks in the stress concentration area behind the tunnel face of the tunnel in high asymmetric in-situ stresses is easier to be influenced by the blasting construction of the tunnel face, and the embodiment customizes large-range triaxial vibration sensors to monitor the blast vibration velocity and acceleration in three directions inside the surrounding rocks; in the embodiment, the customized large-range triaxial vibration sensors are installed at the surface layer point a, the inward surface layer point b and the deeper layer point c of each drill hole using customized connecting pipes from inside to outside as shown in FIG. 6; hole drilling debris, cement and water are mixed to form a sealing material, and a pump is used to transport the sealing material to the drill holes to seal the triaxial vibration sensors, so that the triaxial vibration sensors are integrated with the inner parts of the surrounding rocks of the tunnel in high asymmetric in-situ stresses to ensure that the triaxial vibration sensors and the surrounding rocks of the tunnel in high asymmetric in-situ stresses are consistent in the vibration velocity and acceleration, and after 7 days of solidification, the sealing material is consistent with the surrounding rocks of the stress concentration area in wave impedance.

Step 4: the blast vibration velocity and acceleration measured by each triaxial vibration sensor at the position of the triaxial vibration sensor are collected and stored.

During the blasting construction of the tunnel face in the embodiment, a cloud platform is used to remotely control the triaxial vibration sensors to set relevant parameters, and collect and store the blast vibration velocity and acceleration in three directions at different depths inside the stress concentration area behind the tunnel face during the construction blasting of the tunnel face.

In order to intuitively reflect the damage and destruction degree in the stress concentration area behind the tunnel face of the tunnel in high asymmetric in-situ stresses, the data collected and stored based on the cloud platform comprises the blast vibration velocity and acceleration in three directions at the position of each triaxial vibration sensor, the horizontal distance between the corresponding sensor and the tunnel face, the radial depth of the sensor, and the blasting related parameters of the tunnel face, and a blast vibration propagation model for the tunnel in high asymmetric in-situ stresses is established.

The blast vibration propagation model of the tunnel in high asymmetric in-situ stresses is expressed using the following formula:

$$V = K\left(\frac{Q^{1/3}}{R}\right)^a$$

In the formula, V represents a calculated value of the blast vibration velocity, cm/s; Q represents a quantity of explosives that cause the blast vibration, kg; R represents a blasting distance, m; K and a are respectively a coefficient and an attenuation index related to the physical and mechanical parameters and geological conditions of the surrounding rocks in the stress concentration area behind the tunnel face of the tunnel in high asymmetric in-situ stresses.

The above R is calculated using the following formula:

$$R=\sqrt{L^2+D^2}.$$

Wherein L is a horizontal distance between the tunnel face and the triaxial vibration sensors, and D is a vertical distance between the tunnel wall and the triaxial vibration sensors, which is a depth of the drill holes.

After the establishment of the above blast vibration propagation model, the calculated values of the blast vibration velocities at different positions in the stress concentration area of the rear surrounding rocks during the blasting construction of the tunnel face of the tunnel in high asymmetric in-situ stresses can be obtained. Based on the critical vibration velocity of cracks generated in the surrounding rocks measured by the triaxial vibration sensors, the damage and failure range of the stress concentration area can be determined, then the stability of the surrounding rocks in the stress concentration area of the tunnel in high asymmetric in-situ stresses can be evaluated, further the support parameters at different horizontal distances and different radial depths are determined, and a more accurate scientific basis is provided for excavation and support.

It can be seen that the above method for monitoring the blast vibration velocity can provide a theoretical basis for evaluating the safety of the stress concentration area and support parameters at different radial depths during blasting construction of the tunnel in high asymmetric in-situ stresses.

The invention further provides a system for a blast-induced vibration monitoring of a tunnel in high asymmetric in-situ stresses. The system comprises a plurality of triaxial vibration sensors which are fixed in areas having different radial depths inside surrounding rocks of a stress concentration area behind the tunnel face of the tunnel in high asymmetric in-situ stresses, and each triaxial vibration sensor is used for monitoring blast vibration velocity and acceleration at a position of the triaxial vibration sensor. As described above, firstly, the position of the stress concentration area behind the tunnel face of the tunnel in high asymmetric in-situ stresses, and different radial depths inside the surrounding rocks of the stress concentration area are determined; then, a plurality of drill holes extending from tunnel walls to the inner parts of the surrounding rocks are formed in the stress concentration area behind the tunnel face; in the embodiment, the drill holes are formed in the stress concentration area behind the tunnel face, as shown in FIG. 6, five drill holes of 1#, 2#, 3#, 4# and 5# are formed in a row at an interval of 10 m in the stress concentration area behind the tunnel face, are located in a middle position of the stress concentration area behind the tunnel face, a first drill hole away from the tunnel face is 2 times a tunnel span, the diameter of each drill hole is slightly larger (such as 0.11 m-0.13 m) than the diameter of each triaxial vibration sensor, and the depth of the drill holes reaches a certain depth (such as 1 m) after reaching the deeper layer point c; and then, a sealing material is used for fixing the triaxial vibration sensors in the areas having different radial depth of each drill hole, and the sealing material is formed by mixing drilling debris with cement and water.

Figure 7:
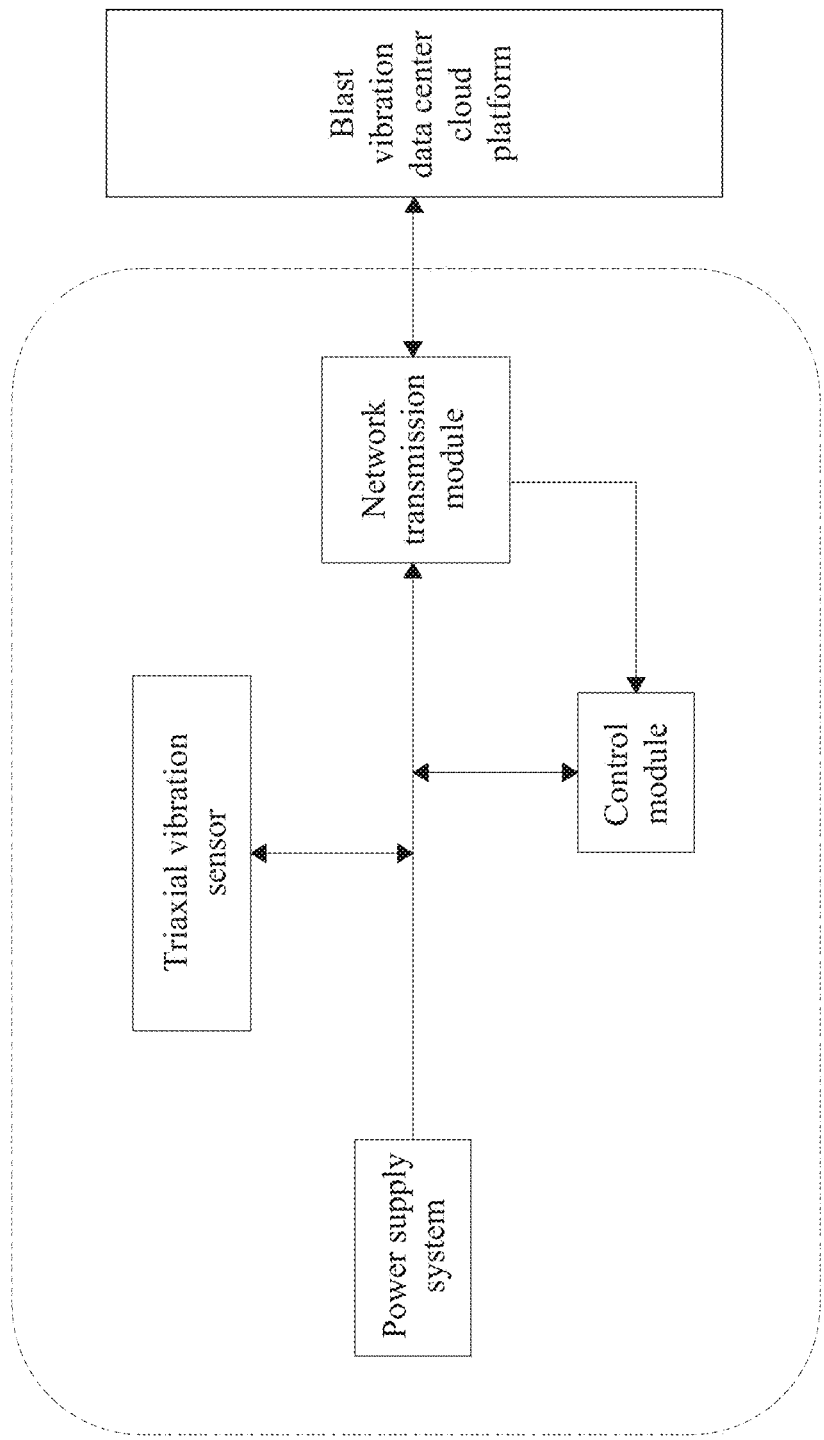
FIG. 7 is a schematic diagram of a system for a blast-induced vibration monitoring of a tunnel in high asymmetric in-situ stresses according to an embodiment of the present invention.

Before blasting, as shown in FIG. 7, the cloud platform is used for controlling the collecting time, sensor positions and other related parameters of the triaxial vibration sensors; after each blast vibration test is completed, the cloud platform is used for collecting and storing blast vibration data in different directions where each triaxial vibration sensor is located, and detailed information such as the magnitude and the direction of the geostress, the size and the shape of an excavation section, blasting time, blasting position, drill-hole arrangement, the number of drill-holes, charging amount, charging structure and detonator segments is recorded.

Through the blast vibration velocity and acceleration in the rear stress concentration area, generated by the blasting of the tunnel face and collected by the triaxial vibration sensors, the blast vibration velocity and acceleration inside the stress concentration area at the positions of the triaxial vibration sensors are directly reflected.

Through the each-time blast vibration data (the blast vibration velocity and acceleration in three directions at the position of each triaxial vibration sensor, the horizontal distance and the radial depth of the corresponding sensor, and the blasting parameters of the tunnel face) recorded by the cloud platform, a blast vibration propagation model for the tunnel in high asymmetric in-situ stresses is established. After the establishment of the blast vibration propagation model, the blast vibration velocities at different positions in the stress concentration area of the rear surrounding rocks during the blasting construction of the tunnel face of the tunnel in high asymmetric in-situ stresses can be calculated. Based on the critical vibration velocity of cracks generated in the surrounding rocks, the damage and failure range of the stress concentration area can be determined, then the stability of the surrounding rocks in the stress concentration area of the tunnel in high asymmetric in-situ stresses can be evaluated, further the support parameters at different horizontal distances and different radial depths are determined, and a more accurate scientific basis is provided for excavation and support.

The method and system of the invention focus on monitoring blast vibration velocity and acceleration at different radial depths in the stress concentration area behind the tunnel face of the tunnel in high asymmetric in-situ stresses. By analyzing monitored data, blasting charging amount, the number of segments, segment differences, drill-hole arrangement and other parameters are optimized. If necessary, an excavation method is adjusted. According to the blast vibration velocity and acceleration at different radial depths, corresponding support parameters, including the thickness of a surrounding rock grouting ring and the length of an anchor rod, can also be determined, the safety and the construction efficiency of tunnel excavation construction are improved, and the safety of construction personnel and equipment is ensured.

The above illustrates one embodiment of the invention in detail. Apparently, the above embodiments are merely a part rather than all of the embodiments of the invention; the embodiments are merely intended to explain the invention, rather than to limit the protection scope of the invention. All other embodiments obtained by a person skilled in the art based on the above embodiments without creative efforts, i.e., all modifications or equivalent substitutions and improvements made within the spirit and principles of the application, shall fall within the protection scope of the invention.

What is claimed is:

1. A method for a blast-induced vibration monitoring of a tunnel in high asymmetric in-situ stresses, comprising:
    fixing triaxial vibration sensors respectively in areas having different radial depths inside surrounding rocks of a stress concentration area behind a tunnel face of the tunnel in high asymmetric in-situ stresses; and
    monitoring blast vibration velocity and acceleration by each triaxial vibration sensor at a position thereof,
    wherein the different radial depths are depths at three places of surface layers, inward surface layers and deeper layers inside the surrounding rocks of the stress concentration area; and
    wherein based on geological data of the surrounding rocks of the tunnel in high asymmetric in-situ stresses, a position of the stress concentration area of a cross section behind the tunnel face of the tunnel in high asymmetric in-situ stresses and the different radial depths inside the surrounding rocks of the stress concentration area are determined according to a geostress distribution of asymmetric virgin rocks and geometric characteristics of the cross section of the tunnel in high asymmetric in-situ stresses.

2. The method according to claim 1, further comprising the following steps:
    Step 1: determining the position of the stress concentration area behind the tunnel face of the tunnel in high asymmetric in-situ stresses, and the different radial depths inside the surrounding rocks of the stress concentration area;
    Step 2: forming a plurality of drill holes extending from walls to inner parts of the surrounding rocks in the stress concentration area behind the tunnel face;
    Step 3: fixing the triaxial vibration sensors respectively in the area having the different radial depths in each drill hole; and
    Step 4: collecting and storing the blast vibration velocity and acceleration measured by each triaxial vibration sensor at the position thereof.

3. The method according to claim 2, wherein five drill holes of $1^\#$, $2^\#$, $3^\#$, $4^\#$ and $5^\#$ are formed in a row at an interval of 10 m in a middle position of the stress concentration area behind the tunnel face.

4. The method according to claim 3, wherein a first drill hole away from the tunnel face is 2 times a tunnel span.

5. The method according to claim 2, wherein the step of fixing the triaxial vibration sensors in the area having the different radial depths in each drill hole comprises steps of mixing hole drilling debris with cement and water to form a sealing material, and using a pump to transport the sealing material to the drill holes to seal the triaxial vibration sensors, so that the triaxial vibration sensors are integrated with the inner parts of the surrounding rocks of the tunnel in high asymmetric in-situ stresses to ensure that the triaxial vibration sensors and the surrounding rocks of the tunnel in high asymmetric in-situ stresses are consistent in the blast vibration velocity and acceleration.

\* \* \* \* \*